US006496728B2

(12) United States Patent
Li et al.

(10) Patent No.: US 6,496,728 B2
(45) Date of Patent: Dec. 17, 2002

(54) METHODS FOR EXTRACTING SUBSTANCES USING ALTERNATING CURRENT

(75) Inventors: S. Kevin Li, Salt Lake City, UT (US); William I. Higuchi, Salt Lake City, UT (US); Honggang Zhu, Salt Lake City, UT (US); Yang Song, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 66 days.

(21) Appl. No.: 09/783,696

(22) Filed: Feb. 13, 2001

(65) Prior Publication Data

US 2001/0044617 A1 Nov. 22, 2001

Related U.S. Application Data

(60) Provisional application No. 60/184,119, filed on Feb. 18, 2000, and provisional application No. 60/244,088, filed on Oct. 28, 2000.

(51) Int. Cl.[7] .................................................. A61B 5/05
(52) U.S. Cl. .......................................... 604/20; 128/803
(58) Field of Search ............................. 604/20; 128/803

(56) References Cited

U.S. PATENT DOCUMENTS

| | | |
|---|---|---|
| 3,991,755 A | 11/1976 | Vernon et al. |
| 4,141,359 A | 2/1979 | Jacobsen et al. |
| 4,325,367 A | 4/1982 | Tapper |
| 4,340,047 A | 7/1982 | Tapper et al. |
| 4,406,658 A | 9/1983 | Lattin et al. |
| 4,689,039 A | 8/1987 | Masaki |
| 4,702,732 A | 10/1987 | Powers et al. |
| 4,734,090 A | 3/1988 | Sibalis |
| 4,752,285 A | 6/1988 | Petelenz et al. |
| 4,764,164 A | 8/1988 | Sasaki |

(List continued on next page.)

FOREIGN PATENT DOCUMENTS

| | | |
|---|---|---|
| DE | 41 37 960 A1 | 5/1993 |
| EP | 0 254 166 A2 | 1/1988 |
| EP | 0 266 083 A1 | 5/1988 |
| EP | 0 308 572 A2 | 3/1989 |

(List continued on next page.)

OTHER PUBLICATIONS

Li, et al., *Pore Induction in Human Epidermal Membrane During Low to Moderate Voltage Iontophoresis: A Study Using AC Iontophoresis*, Journal of Pharmaceutical Sciences, vol. 88, No. 4, pp. 419–427.

Dalziel, et al., *Let–Go Currents and Voltages*, AIEE Transactions, vol. 75, May 1956.

(List continued on next page.)

Primary Examiner—Philippe Derakshani
(74) Attorney, Agent, or Firm—Townsend and Townsend and Crew LLP

(57) ABSTRACT

A variety of methods for extracting different substances such as endogenous substances, pharmaceutical substances, markers of disease, and their metabolites across a tissue are provided. The methods utilize an AC signal to maintain a substantially constant electrical state in a region of the tissue through which extraction occurs, thereby allowing substances to be transported across the tissue in a controlled and predictable manner. Certain methods include an optional AC or DC prepulse signal to initially achieve the target electrical state. An optional DC offset signal can also be utilized to assist in promoting extraction of the substance. The methods have utility in a variety of different clinical settings and applications.

54 Claims, 5 Drawing Sheets

U.S. PATENT DOCUMENTS

| | | |
|---|---|---|
| 4,786,278 A | 11/1988 | Masaki |
| 4,792,702 A | 12/1988 | Masaki |
| 4,850,956 A | 7/1989 | Bontemps |
| 4,931,046 A | 6/1990 | Newman |
| 5,002,527 A | 3/1991 | Reller et al. |
| 5,006,108 A | 4/1991 | LaPrade |
| 5,013,293 A | 5/1991 | Sibalis |
| 5,019,034 A | 5/1991 | Weaver et al. |
| 5,023,085 A | 6/1991 | Francoeur et al. |
| 5,036,861 A | 8/1991 | Sembrowich et al. |
| 5,042,975 A | 8/1991 | Chien et al. |
| 5,047,007 A | 9/1991 | McNichols et al. |
| 5,056,521 A | 10/1991 | Parsons et al. |
| 5,057,072 A | 10/1991 | Phipps |
| 5,140,985 A | 8/1992 | Schroeder et al. |
| 5,213,568 A | 5/1993 | Lattin et al. |
| 5,224,927 A | 7/1993 | Tapper |
| 5,279,543 A | 1/1994 | Glikfeld et al. |
| 5,312,325 A | 5/1994 | Sibalis |
| 5,314,502 A | 5/1994 | McNichols et al. |
| 5,318,514 A | 6/1994 | Hofmann |
| 5,328,452 A | 7/1994 | Sibalis |
| 5,328,453 A | 7/1994 | Sibalis |
| 5,328,454 A | 7/1994 | Sibalis |
| 5,336,168 A | 8/1994 | Sibalis |
| 5,362,307 A | 11/1994 | Guy et al. |
| 5,372,579 A | 12/1994 | Sibalis |
| 5,391,195 A | 2/1995 | Van Groningen |
| 5,395,310 A | 3/1995 | Untereker et al. |
| 5,405,317 A | 4/1995 | Myers et al. |
| 5,415,629 A | 5/1995 | Henley |
| 5,421,817 A | 6/1995 | Liss et al. |
| 5,423,739 A | 6/1995 | Phipps et al. |
| 5,443,441 A | 8/1995 | De Claviere |
| 5,465,713 A | 11/1995 | Schoendorfer |
| 5,499,967 A | 3/1996 | Teillaud et al. |
| 5,538,503 A | 7/1996 | Henley |
| 5,571,149 A | 11/1996 | Liss et al. |
| 5,617,851 A | 4/1997 | Lipkovker |
| 5,620,580 A | 4/1997 | Okabe et al. |
| 5,645,526 A | 7/1997 | Flower |
| 5,658,247 A | 8/1997 | Henley |
| 5,667,487 A | 9/1997 | Henley |
| 5,676,144 A | 10/1997 | Schoendorfer |
| 5,722,397 A | 3/1998 | Eppstein |
| 5,730,714 A | 3/1998 | Guy et al. |
| 5,771,890 A * | 6/1998 | Tamada .................. 604/20 |
| 5,817,012 A | 10/1998 | Schoendorfer |
| 5,827,181 A | 10/1998 | Dias et al. |
| 5,885,211 A | 3/1999 | Eppstein et al. |
| 5,899,876 A | 5/1999 | Flower |
| 5,911,223 A | 6/1999 | Weaver et al. |
| 5,928,571 A | 7/1999 | Chan |
| 5,944,662 A | 8/1999 | Schoendorfer |
| 5,947,921 A | 9/1999 | Johnson et al. |
| 5,954,685 A | 9/1999 | Tierney |
| 5,968,006 A | 10/1999 | Hofmann |
| 5,978,701 A | 11/1999 | Johnson et al. |
| 5,983,131 A | 11/1999 | Weaver et al. |
| 5,989,409 A | 11/1999 | Kurnik et al. |
| 5,991,655 A | 11/1999 | Gross et al. |
| 5,997,501 A | 12/1999 | Gross et al. |
| 6,006,130 A | 12/1999 | Higo et al. |
| 6,010,613 A | 1/2000 | Walters et al. |
| 6,018,679 A | 1/2000 | Dinh et al. |
| 6,023,629 A * | 2/2000 | Tamada .................. 604/20 |
| 6,041,252 A | 3/2000 | Walker et al. |
| 6,041,253 A | 3/2000 | Kost et al. |
| 6,048,337 A | 4/2000 | Svedman |

FOREIGN PATENT DOCUMENTS

| | | |
|---|---|---|
| EP | 0 468 636 A1 | 1/1992 |
| EP | 0 847 775 A1 | 6/1998 |
| GB | 2 177 928 A | 2/1987 |
| JP | 409276416 A | 10/1977 |
| JP | 402124176 A | 5/1990 |
| JP | 402243168 A | 9/1990 |
| JP | 403045272 A | 2/1991 |
| JP | 405049702 A | 3/1993 |
| JP | 407067971 A | 3/1995 |
| JP | 408052224 A | 2/1996 |
| JP | 408322948 A | 12/1996 |
| JP | 411019226 A | 1/1999 |
| WO | WO 88/00846 A1 | 2/1988 |
| WO | WO 91/15256 A1 | 10/1991 |
| WO | WO 91/15257 A1 | 10/1991 |
| WO | WO 92/18197 A1 | 10/1992 |
| WO | WO 94/05368 A1 | 3/1994 |
| WO | WO 94/28967 A1 | 12/1994 |
| WO | WO 97/07853 A1 | 3/1997 |
| WO | WO 98/14235 A1 | 4/1998 |
| WO | WO 99/30773 A1 | 6/1999 |
| WO | WO 99/43383 A1 | 9/1999 |
| WO | WO 99/52589 A1 | 10/1999 |

OTHER PUBLICATIONS

Dalziel, et al., *Effect of Frequency On Perception Currents, AIEE Transactions*, vol. 69, 1950, pp. 1162–1168.

Higuchi, et al., *Mechanistic Aspects of Iontophoresis In Human Epidermal Membrane, Journal of Controlled Release*, 62 (1999), pp. 13–23, Elsevier Science B.V.

Sharma, et al., *Transdermal Drug Delivery Using Electroporation. II. Factors Influencing Skin Reversibility In Electroporative Delivery of Terazosin Hydrochloride in Hairless Rats, Journal of Pharmaceutical Sciences*, vol. 89, No. 4, Apr. 2000, pp. 536–544, Wiley–Liss, Inc,. and American Pharmaceutical Association.

Kim, et al., *Convective Solvent Flow Across the Skin During Iontophoresis, Pharmaceutical Research*, vol. 10, No. 9, pp. 1315–1319, 1993, Plenum Publishing Corporation.

Delgado–Charro, et al., *Characterization of Convective Solvent Flow During Iontophoresis, Pharmaceutical Research*, vol. 11, No. 7, pp. 929–935, 1994, Plenum Publishing Corporation.

Van Der Geest, et al., *Iontophoresis of Bases, Nucleosides, and Nucleotides, Pharmaceutical Research*, vol. 13, No. 4, pp. 553–558, 1996, Plenum Publishing Corporation, 1996.

Peck, et al., *Flux Enhancement Effects of Ionic Surfactants Upon Passive and Electroosmotic Transdermal Transport, Journal of Pharmaceutical Sciences*, vol. 87, No. 9, pp. 1161–1169, Sep. 1998, American Chemical Society and American Pharmaceutical Association, 1998.

Li, et al., *Lag Time Data for Characterizing the Pore Pathway of Intact and Chemically Pretreated Human Epidermal Membrane, International Journal of Pharmaceutics*, 170, pp. 93–108, 1998, USA.

Li, et al., *Pore Charge Distribution Considerations In Human Epidermal Membrane Electroosmosis, Journal of Pharmaceutical Sciences*, vol. 88, No. 10, pp. 1044–1049, American Chemical Society and American Pharmaceutical Association, 1999.

Li, et al., *Characterization of the Transport Pathways Induced During Lower to Moderate Voltage Iontophoresis in Human Epidermal Membrane, Journal of Pharmaceutical Sciences*, vol. 87, No. 1, pp. 40–48, American Chemical Society and American Pharmaceutical Association, 1998.

Copy of International Search Report for PCT/US 01/04640.

* cited by examiner

METHODS FOR EXTRACTING SUBSTANCES USING ALTERNATING CURRENT

CROSS-REFERENCES TO RELATED APPLICATIONS

This application claims the benefit of U.S. Provisional Application No. 60/184,119, filed Feb. 18, 2000, and U.S. Provisional Application No. 60/244,088, filed Oct. 28, 2000, both of which are incorporated herein in their entirety for all purposes. This application is also related to U.S. application Ser. No. 09/783,138, filed Feb. 13, 2001, which claims the benefit of U.S. Provisional Application No. 60/244,116, filed Oct. 28, 2000, both of which are also incorporated herein in their entirety for all purposes.

STATEMENT AS TO RIGHTS TO INVENTIONS MADE UNDER FEDERALLY SPONSORED RESEARCH AND DEVELOPMENT

This invention was made with support from Grant Number GM 43181 awarded by the National Institutes of Health. Therefore, the government has certain rights in this invention.

FIELD OF THE INVENTION

This invention relates generally to the field of substance extraction and detection from a subject's body utilizing electrical signals, including substances extracted by iontophoresis.

BACKGROUND OF THE INVENTION

The transport of various agents such as metabolites, drugs and nutrients across tissues is a function primarily of three factors: tissue permeability, the presence or absence of a driving force and the size of the area through which transport occurs. The lack of inherent permeability of many molecular permeants severely impedes the movement of permeants across a layer of tissue. Permeability in skin is low because the unique, tightly packed arrangement of cells in the membrane and the intercellular lipid matrix make the *stratum corneum* relatively impermeable, especially to polar and ionized species.

Iontophoresis is one method that has been explored as a way to effectuate transport of agents across a tissue. Such methods have been used primarily to deliver rather than extract agents through a tissue into the body (e.g., transdermal delivery of a drug). Iontophoresis is characterized by the application of an electrical current to enhance transport across a tissue by driving ionized agents through the membranes as a result of a direct electrical field effect (e.g., electrophoresis), electroosmosis, or through electrically induced pore formation (electroporation). In practice, iontophoretic methods generally involve positioning an electrode that includes some type of reservoir on the tissue through which delivery is to occur. The reservoir typically includes a solution or an absorbent pad that contains the substance to be transferred. This is called the active or drug electrode. Another electrode is also placed in contact with the tissue to allow for the completion of the electrical circuit. This is called the return, inactive, or indifferent electrode.

Application of a voltage between the two electrodes and across the tissue generates a current that causes the ionized agent of one charge to move towards the electrode of the opposite charge. In the standard configuration in which iontophoresis is used to deliver an agent, this current drives the agent in the reservoir at the active electrode through the tissue and into the body. Neutral agents can also be transported, albeit less effectively than ionized agents, via electroosmosis. The electric field also induces new pore formation on the tissue and increases its permeability. When the tissue is skin, the agent penetrates the *stratum corneum* and passes into the dermo-epidermal layer. The outermost portion of the dermis layer is typically referred to as the papillary layer and contains a network of capillaries from the vascular system. This network absorbs the agent and subsequently moves it to the main portion of the vascular system.

During analyte extraction, with the analyte traverses the membrane outward from the dermo-papillary layer to the surface of the *stratum corneum* under the influence of an electrical field. When iontophoresis is used to extract a substance from a body, the reservoir is the site at which the substance is collected. The current formed between the electrodes acts to extract the substance from the vascular network through the tissue and into the reservoir.

A majority of iontophoretic methods utilize constant-current DC signals to effectuate transport. There are several problems associated with such methods that have resulted in limited acceptance by regulatory authorities, clinicians, and patients. Literature and unpublished data from the inventors' laboratories suggest that one shortcoming of constant-current DC is the inability to achieve a constant flux at constant current due to time-dependent changes in tissue porosity, accompanying changes in pore surface charge density and effective pore size over the course of treatment. Such changes and the resulting flux variability pose significant problems in effectively controlling the transport (either delivery or extraction) of agents through a tissue by iontophoresis. It is generally known that with constant-current DC methods the transference number (fraction of total current carried by a particular charged species) for the bioactive agent changes with time over the course of a typical iontophoresis procedure. Thus, while application of the DC signal initially results in a state of electroporation, with time the properties of the pores change. This trend can be monitored by the changes in the tissue electrical resistance and/or the changes in the transference number with time during iontophoretic transport. This variability in transference number means that the amount of agent transported across a tissue varies with time and cannot be controlled, monitored, nor predicted effectively. Problems in controlling the extent of electroporation with constant-current DC methods also result in high inter- and intra-patient variability. Hence, not only does the amount of agent transported vary as a function of time, there is further day-to-day variation for the same individual, as well as variation from person to person.

Yet another problem is a function of byproducts formed during iontophoresis. With many direct current systems, transport is accompanied by water hydrolysis that causes significant pH shifts at the electrodes. In particular, protons accumulate at the anode while hydroxide ion accumulates at the cathode. Such pH shifts result in electrochemical burns that can cause tissue damage. In addition, water hydrolysis results in gas formation that interferes with the contact, and hence the electrical conduction, between the electrode components and tissue surface. The use of pure AC ameliorates water hydrolysis and subsequent problems with tissue irritation and gas formation.

Various strategies have been tested to address these problems, including the use of different wave-forms and pulsed DC signals rather than constant-current signals. It has been suggested that the use of pulsed DC signals should theoretically provide improved performance by allowing skin capacitance to discharge, thereby allowing for more controlled current flow and agent transport. However, many DC pulsed methods suffer from at least some of the same general problems as the constant-current DC methods.

The following U.S. patents are illustrative of general pulsed DC methods: U.S. Pat. No. 5,391,195 to Van Groningen; U.S. Pat. No. 4,931,046 to Newman; and U.S. Pat. No. 5,042,975 to Chien et al. Certain DC methods employ a combination of pulsed and continuous electric fields (see, e.g., U.S. Pat. No. 5,968,006 to Hofmann). Each of the foregoing patents, however, are limited in that they discuss only methods for delivering substances across a tissue into the body of an individual. These patents include no discussion of methods for extracting compounds from a body across a tissue. Furthermore, these patents only discuss the use of DC signals to perform iontophoresis; the patents include no discussion on how AC signals can be utilized to effectuate transport. In particular, these patents do not discuss how to maintain a substantially constant electrical state in order to maintain substantially constant levels of transport (e.g., a transference number) for the substance(s) being transported.

The iontophoretic literature on balance has taught against the utility of AC signals in conducting iontophoresis. It has been the belief of many of those skilled in the art that an AC signal lacks the necessary driving force to achieve effective iontophoretic transport; instead, the view has been that the driving force of an applied DC signal is required to transport a charged species. The bidirectional nature of an AC signal, led many to conclude that the use of an AC signal would result in inefficient transport at best, and perhaps no net transfer at all. For example, in U.S. Pat. No. 5,391,195 it is noted that "the negative pulse [of an alternating current] would result in an inverse effect to the positive pulse, thereby reducing the efficiency of treatment."

Nonetheless, certain investigators have discussed the use of AC signals for specific purposes in conducting iontophoresis. For example, several patents to Sabalis (see, e.g., U.S. Pat. Nos. 5,312,325; 5,328,454; 5,336,168; and 5,372,579) discuss systems in which a current oscillator is utilized to apply periodic electrical variations to the skin of a patient, the goal being to trigger rhythmical variations of the potential and resistance of the skin that reinforce the natural delivery rhythms of the individual being treated. Some discuss the use of AC signals as a way to more efficiently deliver multiple substances (e.g., a drug and a substance that inhibits blood clot formation) having opposite charges (see, e.g., U.S. Pat. No. 5,328,453). Others have discussed methods that involve application of a series of separate or overlapping waveforms that can include an AC component (see, e.g., U.S. Pat. Nos. 5,135,478 and 5,328,452 to Sabalis, and U.S. Pat. No. 5,421,817 to Liss et al). Liss et al., however, reinforced the view that the use of an AC signal is not preferred, noting that a reversal in polarity will "tend to reverse or slow the transdermal delivery of the drug."

There has also been some discussion in the literature regarding the use of AC signals in iontophoresis to minimize the electrochemical burns that can occur with DC methods (see, e.g., Howard et al., (1995) Arch. Phys. Med. Rehabil. 76:463–466; and U.S. Pat. No. 5,224,927 to Tapper). The use of AC signals to control and reduce skin irritation after passive or iontophoretic transport of a drug has also been discussed (see, e.g., Okabe et. al., Journal of Controlled Release, Volume 4, Year 1986, pages 79–85), as has the use of AC signals in related methods such as in the treatment of hyperhidrosis (see, e.g., Reinauer, et al. (1993) Br. J. Derm. 129:166–169). Some researchers (see, e.g., U.S. Pat. No. 6,018,679 to Dinh) have examined the use of a brief current reversal as a means of withdrawing potentially irritating compounds from the tissue following their iontophoretic delivery.

However, none of these patents or articles discuss the issue or problems of extracting substances from a body across a tissue. Instead, these patents and publications focus on delivery of an agent into the body of an individual. Additionally, none of these patents or publications discuss the use of an AC signal to maintain a substantially constant electrical state to control extraction in a predictable fashion.

A limited number of patents discuss certain methods of using iontophoresis in extraction of a substance from the body of an individual across a tissue. U.S. Pat. No. 5,019,034 to Weaver et al. discusses methods that utilize a series of short DC pulses to induce electroporation, in particular a state referred to as reversible electrical breakdown. Various forces can then be utilized to effectuate extraction of a substance across a tissue. Once electroporation is established, the nature of the DC pulses (e.g., pulse duration, shape and frequency) is maintained until transfer is complete. U.S. Pat. Nos. 5,730,714 and 5,362,307 to Guy et al. and U.S. Pat. No. 5,279,543 to Glikfeld et al. discuss methods for extracting and delivering substances by iontophoresis utilizing an apparatus characterized by a particular electrode arrangement. U.S. Pat. Nos. 5,771,890 and 6,023,629 to Tamada discuss particular methods in which the direction of a direct current is periodically reversed during sampling of a substance. The frequency of current reversal discussed in the '890 and '629 patents is typically very low, tending to fall within the range of 1 cycle per 20 seconds to about 1 cycle per 4 hours. The methods discussed by Guy et al. and Glikfeld et al. are limited to DC methods and Weaver et al. discuss only DC pulse methods. As with all the foregoing patents and publications, Weaver et al., Guy et al., Glikfeld et al. nor Tamada discuss the use of an AC signal to maintain a substantially constant electrical state.

Thus, none of the foregoing patents and articles address the challenge of maintaining a substantially constant electrical state and a substantially constant electroporative state such that transport of a substance across the tissue, and particularly extraction of a substance, occurs in a predictable and controlled fashion during the time period for transport. Nor is there a discussion of methods for reducing intra- and inter-subject variability that plagues many iontophoretic methods.

SUMMARY OF THE INVENTION

Methods for extracting different substances across a tissue utilizing an AC signal are provided. The methods can be utilized to extract a number of different substances such as endogenous substances located within the body of an individual, pharmaceutical substances, markers of disease and metabolites. During the extraction process, the AC signal is used to maintain a substantially constant electrical state in a region of the tissue through which extraction occurs, thereby allowing substances to be transported across the tissue in a controlled and predictable manner. The methods have utility in a wide range of applications. For example, certain methods can be utilized in various therapeutic treatments to monitor the level of a metabolite or pharmaceutical agent. Other methods can be utilized in diagnostic applications to detect the presence of a disease marker, for instance.

Thus, certain methods more specifically involve extracting a substance from a body through a tissue by supplying one or more electrical signals, one of which is an AC signal that is applied to the tissue. The AC signal is then adjusted so as to maintain a substantially constant electrical state within a region of the tissue, wherein maintenance of the substantially constant electrical state facilitates extraction of the substance. The AC signal is typically adjusted to maintain a substantially constant state of electroporation in the region of the tissue throughout the time period in which the substance is extracted. With some methods, the electrical state that is maintained by the AC signal is an electrical conductance or electrical resistance. The AC signal applied to the tissue can have essentially any waveform. The waveform can be symmetric or asymmetric, thus including square, sinusoidal, saw-tooth, triangular and trapezoidal shapes, for example. The frequency of the AC signal tends to be at least about 1 Hz, although in other instances the frequency is within the range of about 1 Hz to about 1 kHz, or about 1 kHz to about 30 kHz.

Other extraction methods include an optional electrical prepulse applied to the tissue prior to the AC signal to induce electroporation within the region of the tissue through which extraction is to occur. The prepulse can be either an AC signal or a DC signal. The voltage of the prepulse generally is in the range of about 1 to about 90 V, in other instances about 5 to about 20 V, in still other instances about 20 to about 40 V, and in yet other instances about 40 to about 90 V. The actual voltage can be any particular voltage or span of voltages within these ranges.

Extraction of the substance across the tissue can be via passive diffusion through an electroporated region induced by the AC signal. Certain methods, however, utilize an optional DC offset signal that is applied to the tissue in combination with the AC signal. The DC offset signal is effective to promote extraction of the substance through the region maintained at a substantially constant electrical state. The DC offset signal is typically applied substantially continuously during extraction of the substance and is of a voltage or current, effective to control the rate of extraction. The DC offset signal is usually in the range of about 0.1 to 5 V and about 0.01 to 0.5 mA/cm$^2$, but can include any particular voltage, current or span of voltages or currents within this range. In certain methods, the DC offset signal is applied utilizing two electrodes in contact with the tissue and the direction of current flow of the DC offset signal is periodically reversed between the two electrodes.

Still other methods combine both the prepulse and the DC offset with the AC signal to extract substances across a tissue. Such methods generally involve applying the electrical prepulse to the tissue prior to the AC signal to induce electroporation within the region. The DC offset signal is also applied to the tissue and is effective to promote extraction of the substance through the region maintained at a substantially constant electrical state by the AC signal.

The methods can be utilized with a variety of different types of tissue, including both animal and plant tissues. The tissues can be part of a body surface or can be artificial in nature. Usually the tissue is skin or mucosal tissue, particularly human skin or mucosal tissue. A variety of substances can also be extracted, including charged and uncharged substances.

DETAILED DESCRIPTION

I. Definitions

Figure 1:
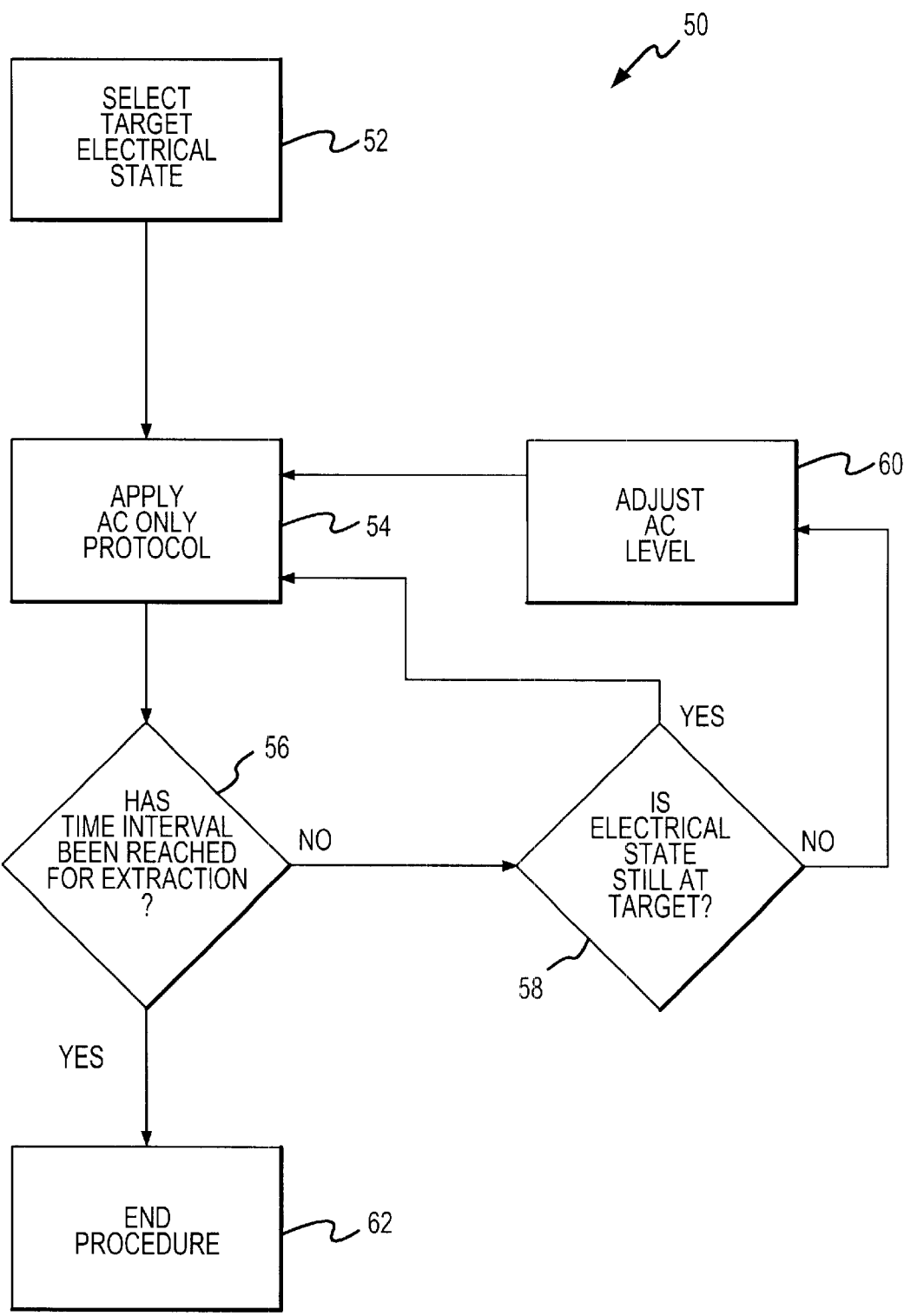
FIG. 1 is a schematic block diagram illustrating steps in a method utilizing only an AC signal to extract a substance across a tissue as provided herein.

Before describing the present invention in detail, it is to be understood that unless otherwise indicated this invention is not limited to specific iontophoretic extraction devices, the substances capable of being monitored, or the like, as such can vary. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise.

In describing and claiming the present invention, the following terminology will be used in accordance with the definitions set out below.

The term "body" when used in reference to an extraction process generally refers to a source containing a substance that is to be extracted across a tissue. Typically, a body refers to the body of an animal, most typically the body of a human. In such instances, the term can include the skin, underlying tissue or the circulating blood.

The term "body surface" is used to refer to skin or mucosal tissue, including the interior surface of body cavities that have a mucosal lining. The term "skin" should be interpreted as including "mucosal tissue" and vice versa.

A "region" of a tissue refers to the region of a tissue that is electroporated via the application of one or more electrical signals and through which a substance is extracted. Thus, a region of a body surface refers to an area of skin or mucosal tissue through which a substance is extracted.

The term "electroporation" generally refers to an increase in tissue permeability believed to be due to the induction and/or increase in pore size and/or number in a tissue through which a substance can be extracted during an iontophoretic process. Thus, the term "electroporative state" refers to the permeability of a tissue that has been electroporated.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The terms "pharmacologically active agent," "pharmaceutical agent," "drug," "and "therapeutic agent" are used interchangeably herein to refer to a chemical material or compound suitable for administration to a subject and that induces a desired effect. The terms include substances that are therapeutically effective as well as substances that are prophylactically effective. The term also encompasses derivatives and analogs of those compounds or classes of compounds specifically mentioned, including active metabolites that also induce the desired effect.

As used herein an "individual" or "subject" includes both human and veterinarian subjects.

II. Overview

A variety of methods that achieve controlled and predictable transport of substances across tissues are disclosed herein. In particular, the methods are used for the extraction of one or more substances from the body of an individual. The methods are based in part upon the recognition that an AC signal alone or in combination with one or more AC or DC signals can be utilized to induce and maintain a substantially constant electrical state in a region of a tissue through which transport occurs. By maintaining such an electrical state, one can maintain the permeability of the tissue within the region such that pore size, pore density and surface charge density within the region is maintained. The process of applying an electrical signal to increase tissue permeability (e.g., to create or enlarge pores within the tissue) is referred to as electroporation, and the degree of permeability so obtained referred to as a state of electroporation.

Controlling tissue permeability or electroporative state in this manner enables one to reduce variability in the flux of a substance across the tissue such that a substantially constant transference number is achieved for the substance being transported. Reduction in flux variability in turn means that one can extract substances such as metabolites, toxins, disease markers or previously administered pharmaceuticals in a controlled and predictable way. Intra- and inter-patient variability in the rate of extraction can also be minimized using certain methods disclosed herein. The electrical state and thus the degree of electroporation of a tissue can be ascertained by monitoring the electrical conductance or resistance of the tissue or by measuring similar electrical parameters that correlate with the degree of tissue permeability.

While the AC signal is adjusted to maintain a substantially constant electrical state, transport of substance across the tissue can be accomplished in various ways. If the concentration of substance on one side of a tissue is significantly higher than the other side of the tissue (e.g., the interior side of skin relative to the exterior side), transport of a substance through the electroporated region can be achieved by passive, Fickian driven, diffusion. Other methods include applying a DC offset of the AC signal to the electroporated region to drive the substance through the region and increase its rate of transport. Certain methods include an optional prepulse to quickly attain a desired electrical state that is then maintained with the AC signal. The prepulse can be either an AC or DC signal. Hence, the methods provided herein can include simply an AC signal ("AC protocol" or "AC-only protocol"), a combination of an AC signal and a DC offset signal ("AC plus DC offset protocol"), either of which can be further combined with an AC or DC prepulse.

The methods provided herein differ significantly from conventional DC or pulsed DC iontophoretic delivery or extraction methods. As described in the background section, a significant shortcoming with constant current DC methods and pulsed DC methods is their failure to maintain a substantially constant state of tissue permeability or electroporation. With direct current, the electrical properties, e.g., electrical resistance within the region of the electroporated tissue changes with time during iontophoresis, accompanying a change in the transport properties of the pores with time. The inability to maintain a substantially constant electroporated state severely limits the ability of constant-current DC methods to controllably and predictably extract an agent across a tissue. For example, in U.S. Pat. Nos. 5,771,890 and 6,023,629 to Tamada, the DC results in a "flux-shift" that must be corrected with population mean mathematical algorithms. The methods of the present invention, by maintaining a substantially constant electrical state during the period in which transport occurs, can ameliorate this problem.

III. Description of Various Methods

A. General

A common feature of the various methods described herein is the use of an AC signal to maintain a substantially constant electrical state so as to limit flux variability in the extraction of substances across a tissue such as a body surface. The electrical state is typically maintained throughout the time period during which extraction occurs. By maintaining a substantially constant electrical state and state of electroporation, the effective pore density, pore size and pore surface charge density remain essentially constant during a treatment procedure. This in turn allows for a substantially constant, controllable and determinable transport rate for the substance being extracted.

As used herein, the term "AC signal" generally refers to an electric signal (e.g., current or voltage) that reverses direction periodically. As described further below, typically the AC signal has a frequency of at least about 1 Hz. The phrase "electrical state" refers to a state that correlates with or is a measure of the permeability of the tissue being electroporated and that can be measured as an electrical value. A substantially constant electrical state correlates with a substantially constant electroporative state. A substantially constant electrical state is evidenced, for example, by a substantially constant resistance or conductance within the region being electroporated, and/or by a substantially constant transference number (fraction of total current carried by a particular substance) for the substance being extracted.

The methods can be used for the controlled and predictable extraction of various substances, including both charged and uncharged species. As is typical in iontophoresis, the permeant primarily tends to be a charged entity. However, the methods described herein are not limited to extraction of charged molecules only. Methods set forth herein can be utilized in the extraction of noncharged substances.

The methods are designed to accomplish extraction of a substance across a tissue and more specifically a region of the tissue. As used herein a "tissue" is defined to mean an aggregation of similar cells or cell components. Often the cells are united in performance of a particular function. The tissue can be part of a living organism, a section excised from a living organism, or can be artificial. An artificial tissue is one in which an aggregation of cells are grown to function similar to a tissue in a living organism. The aggregated cells, however, are not obtained from a host (i.e., a living organism). Artificial tissues can be grown in vivo or in vitro. Human skin, for instance, can be cultured in vitro to obtain an aggregation of cells, of monolayer thickness or greater, that can function as a skin tissue in culture or once grafted onto a living host. Certain types of artificial tissues that can be utilized with certain methods of the invention are discussed, for example, in U.S. Pat. Nos. 4,458,678; 4,485,096; and 4,304,866.

Certain methods are performed with human or animal tissue. Thus, the methods can be utilized in various clinical applications for human patients, as well as veterinarian applications. If performed with animals, the animals can be essentially of any kind provided the animal has a tissue layer into which pores can be generated via the application of an electrical signal. Hence, some methods can be performed, for example, with domestic animals such as dogs and cats; farm animals such as horses, cows, sheep and pigs; exotic animals; reptiles; birds; and amphibians. Still other methods are performed with plants or plant cell cultures.

In some instances the tissue is a body surface of an animal such as a human, particularly skin or mucosal tissue such as lines the oral, nasal, rectal or vaginal cavities or other similar cavities. Thus, the substance can be extracted from the skin, underlying tissue, or the circulating blood into a collection reservoir (see infra).

B. AC Signal

1. General

Certain features of the applied AC signal assist in achieving the goal of maintaining a substantially constant electrical state while avoiding some of the problems associated with DC-based methods. For example, a problem with existing DC transdermal iontophoresis technology is that such methods allow skin resistance to vary over time; this in turn results in a variation in the rate at which agent is extracted through the tissue. The use of an AC signal, however, can reduce this problem. Because the AC component continuously reverses polarity, the tissue remains substantially depolarized throughout the transport procedure and thus is less susceptible to building up charges and changes in pore size.

The AC signal also acts to facilitate transport by inducing the formation of new pores and/or enlarging the existing pores. It has been found by the current inventors that application of an AC signal can generate new pores in tissue without a concomitant enhancement of transport via electroosmosis. Thus, enhanced transport upon application of an AC signal is a consequence, at least in part, of new pore generation. (See, e.g., Li et al. (1999) *J. Pharmaceutical Sciences* 88:419–427, which is incorporated herein by reference). By generating new pores, application of the AC signal can significantly enhance the rate of extraction as compared to passive diffusion alone.

Further, while many individuals skilled in the art have believed that a DC field is required to transport a charged compound and that an AC signal lacks the necessary driving force for iontophoretic transport, the present inventors have discovered that AC iontophoresis does not eliminate the direct-field effect (i.e., electrophoresis) and up to about 10% of this effect remains at a relatively low frequency AC (e.g., 10 Hz to 1 kHz). While not intending to be bound by any particular theory, this AC flux-enhancing phenomena is thought to be a result of unsymmetrical boundary conditions of the targeted substance across the skin. Thus, an AC signal also provides a means to enhance transport of ionic substances via the reduced direct field effect and electroporation without complications from the electrochemical reactions of the electrodes.

There are other benefits that can be obtained from utilization of an AC signal beyond the enhanced level of control during extraction. For instance, application of an AC signal during transport, compared to traditional DC iontophoresis, causes less skin irritation and has a higher threshold of discomfort. That is, using high frequency AC causes less untoward sensation/pain at a given current level than does DC. Thus, the use of an AC field for iontophoresis is better than DC for these issues (see, e.g., Dalziel & Mansfield, AIEE Trans, Year 1950, Volume 69, Pages 1162–1168; and Dalziel & Massoglia, AIEE Trans, Year 1956, Volume 75, Pages 49–56). The frequency, electroporation, and sensation relationships are important for another reason. Results on the frequency effects upon the extent of pore induction in skin show very small dependency of frequency on the extent of pore formation in the low AC frequency region (e.g., 10 to 250 Hz). These results indicates that the dependence of frequency upon pore induction in skin is less than those upon the sensation threshold. Therefore, an optimal AC frequency region can be utilized in AC methods in which a high AC voltage is employed to increase the extent of pore induction and to enhance transport with minimal sensation and irritation.

2. Applying AC Signal to Tissue

As described in greater detail below, application of the AC signal (and optional prepulse and DC offset signal) is typically applied to a tissue using at least one pair of electrodes that are placed in contact with the tissue being treated. At least one electrode includes a reservoir to receive the substance (e.g., metabolite) that is to be extracted. This electrode is positioned over the region of the tissue through which transport is to occur. A second electrode is also placed in contact with the tissue and is positioned to form an electric circuit with a current source. The AC signal can be performed with or without excipients that optimize the conditions for transport of agents across the tissue.

For methods performed with humans, the electrodes are often placed in contact with the outermost skin layer, the *stratum corneum*. Application of the AC signal, combined with an optional prepulse signal, generates and maintains pores within the skin, thereby allowing a substance to be transported across the *stratum corneum* and into the receiving reservoir or compartment.

The applied AC signal is of an appropriate voltage and waveform to effectively induce and/or maintain a desired electrical state, which state is an electroporated state that allows for enhanced transport of the substance relative to unporated tissue. Typically, the target electrical state is a selected electrical resistance or electrical conductance. Alternatively, or in addition, other electrical parameters from which electrical resistance or conductance values can be determined can be monitored, as well as any other parameter that corresponds to the degree of tissue permeability. Typically, the AC signal is applied to maintain the substantially constant electrical state throughout the time period during which extraction of a substance is occurring. The actual period for extraction varies significantly depending upon the nature of the application. Some applications can be performed in about 10 minutes, while other applications may last 12 to 24 hours or more.

During the time which extraction is being performed, the AC signal is varied as needed to maintain the electrical state at a selected target value, or more typically, within a target range. Most typically this is achieved by varying the amplitude and/or frequency of the applied voltage. For methods in which electrical resistance of a patient's skin is monitored, the target resistance may vary somewhat from individual to individual. In general, however, the target resistance tends to be approximately 1–30 $k\Omega \cdot cm^2$, and more typically a value within the range of 5–15 $k\Omega \cdot cm^2$. The target resistance can also be a fixed fraction of the patient's initial resistance. In general, the target resistance is approximately from 0.1 to 10% of the initial resistance, with more typical values within the range of 0.1 to 1%.

The AC signal is typically applied as necessary to maintain the selected target value such that the measured value does not increase or decrease by more than about 20% of the target value. Thus, if the target is 5 $k\Omega.cm^2$, then the AC signal is varied as required to keep the measured resistance within the range of about 4–6 $k\Omega.cm^2$. In certain other methods, the fluctuation is limited to less 10% of the target value, in other methods, less than about 5%, and in still other methods, less than about 1%.

The frequency, waveform and duration of the AC signal can vary as long as it is effective to maintain the selected electrical state within the desired range. In general, however, the frequency of the AC signal tends to be at least about 1 Hz. In certain methods, the applied frequency generally falls within the range of about 1 Hz to about 1 kHz; while in other methods, the frequency usually is within the range of about 1 kHz to about 30 kHz. The actual frequency can be any particular value or range of values within these ranges. A variety of waveforms can be utilized. Suitable waveforms include both symmetric and asymmetric waveforms, including waveforms having square, triangular, sinusoidal, saw-tooth and trapezoidal shapes and the like.

The size of the region of the tissue to which a signal is applied can vary significantly depending upon the nature of the application. In some instances, the region is less than 1 $cm^2$. In general, the region being electroporated and through which substance is extracted tends to be about 1 $cm^2$ to about 200 $cm^2$. The size of the region tends to be smaller in other applications, ranging from about 5 $cm^2$ to about 100 $cm^2$. In still other methods, the region tends to be about 5 $cm^2$ to about 30 $cm^2$. The size of the region can also be any particular value or range of values within these ranges. The shape of the region can be any geometric shape and is not limited to any one particular shape or type of shape.

3. Transport of Neutral Species

Methods utilizing AC signals to perform transport without a DC component can be useful for extracting a neutral substance (e.g., glucose or ethanol) across a tissue. The inventors of the present invention have also found that methods conducted using AC signals at frequencies above about 1 Hz without the application of DC involve little or no electroosmosis. Thus, when performing extractions utilizing only an AC signal, there is negligible electroosmosis. Furthermore, when transporting a neutral agent, there is no electrophoresis. Transport in this situation is similar to passive diffusion but is enhanced due to the induction of new pores (i.e., higher skin porosity) and/or enlarged or increased porosity due to electroporation.

Although transport of neutral substances under AC can result in lower fluxes than with traditional constant current DC systems (due mostly to the absence of electroosmosis), methods using strictly AC signals are nonetheless useful because intra-patient and inter-patient variability associated with variable pore surface charge density is minimized. Additionally, there is no electrostatic partitioning of substances into the skin for neutral permeants and the pore size seems to remain relatively constant. The ability to minimize variations in transfer during the process obviates the need for frequent finger pricking calibrations required by certain existing glucose monitoring devices (e.g. the Glucowatch Biographer™ by Cygnus®). Avoidance of such calibrations should greatly improve patient compliance in the use of monitoring devices (e.g., glucose monitoring).

C. Optional Prepulse

A relatively high-voltage DC or AC prepulse can optionally be applied to the tissue to quickly attain a target electrical state or state of electroporation which is subsequently maintained by adjusting the AC signal as needed. Once the prepulse causes the tissue to reach the desired electrical state, the flux of the substance being extracted can be controlled by maintaining a substantially constant electrical state within the electroporated region utilizing an AC signal (e.g., a substantially constant resistance or conductance). When an AC signal is utilized as a prepulse, this signal can subsequently be utilized to maintain the target electrical state. The AC prepulse can also be followed with a separate AC signal to maintain the target electrical state, typically applied shortly after completion of the prepulse.

While the AC signal alone can be used to reach the desired electrical state, the advantage of using a prepulse is that it can accelerate the process of establishing the desired electrical state. The longer time period associated with using strictly an AC signal alone without a prepulse, however, is still preferable over a DC-only protocol since the AC-only protocol still results in a predictable and stable electrical state that promotes constant transport properties for the tissue, which is not the case when applying DC signals alone.

In general, the characteristics of the AC or DC prepulse are selected to be effective to obtain the desired electrical state. Typically, this means that the prepulse signal is applied to reach a target electrical resistance or conductance. The voltage of the prepulse is often in the range of about 1 to about 90 V. In other methods, the voltage is in the range of about 9 to about 20 V. In still other methods, the voltage is about 20 to about 40 V, while in other methods about 40 to about 90 V.

If an AC prepulse is utilized, the AC prepulse can be symmetric or asymmetric. A variety of suitable AC prepulse waveforms can be used, including, but not limited to, a square waveform, a sinusoidal waveform, a saw-tooth waveform, a trapezoidal waveform and a triangular waveform. The duration of the prepulse is sufficiently long so as to achieve the target electrical state. Duration of the prepulse depends in part upon the voltage of the prepulse. In general, however, the prepulse is typically between 10 microseconds and 20 minutes. If a prepulse is utilized, it too can be DC or supplied in a variety of waveforms wherein the shape of the waveform is square, triangular, trapezoidal or saw-tooth, for example. The prepulse is of sufficient duration to establish the target electrical state.

D. Optional DC Offset Signal

Methods employing the AC signal alone to conduct transport across a tissue involve primarily passive diffusion to achieve transport. As indicated above, however, transport is improved over purely passive transport for both uncharged and charged substances because the AC signal induces electroporation through which a substance can diffuse and specifically for ionic compounds because of the existence of a small direct-field effect associated with AC protocols. To promote extraction and accelerate the extraction process, the AC signal can optionally be combined with a DC offset signal. Methods utilizing this combination are sometimes referred to as an "AC plus DC protocol." With this particular combination of signals, the AC signal is utilized primarily to maintain a region of the tissue at a substantially constant electrical state to maintain a level of permeability that enhances transport. The DC offset signal is applied to further enhance transport and to promote extraction of the substance. Adjusting the AC signal to maintain a constant electrical state generally will not interfere with the DC offset driven transport. With such a combination of signals, a relatively stable rate of extraction of substance across the tissue can be achieved. This contrasts with conventional methods using only DC signals to effectuate transport in which the flux of agent is often unpredictable.

As a general matter, the DC offset signal applied to the tissue is typically effective to maintain a substantially constant rate of extraction of the substance being transferred across the tissue. Thus, the timing and duration of the DC offset signal in general is governed by this goal. The rate at which the substance is extracted can be controlled by the electrical resistance or conductance of the tissue and the DC offset voltage or current.

The DC offset signal is often applied essentially simultaneously with application of the AC signal. This timing is appropriate, for example, when a prepulse has already established the desired electrical state. In other methods, however, the DC offset signal is delayed until after the AC signal has been initiated. A delay may be appropriate, for instance, with methods conducted without a prepulse to allow the AC signal to establish the target electrical state. However, the DC offset can be briefly delayed even for those methods that use a prepulse to initially establish the target electrical state without DC offset interference. Such a delay, if any, is usually relatively brief and typically less than 10 minutes. Normally, the voltage of the DC offset signal is in the range of about 0.1 V to about 5 V, while in other methods the voltage is in the range of about 0.1 to about 2.5 V. The current range is typically 0.01 to about 0.5 mA/cm$^2$.

E. Exemplary Methods

The foregoing electrical signals can be combined in various combinations to yield a variety of different protocols for extracting a substance across a tissue. Exemplary methods follow. While the methods can be conducted with a number of different tissue types and different parameters can be monitored to assess the electrical state of the tissue, often such methods are performed with human tissue and involve monitoring the electrical resistance or conductance of the skin. The following examples are intended to be only illustrative and should not be considered to be limiting.

1. AC-Only Protocol

FIG. 1 illustrates a method 50 that begins with the selection 52 of a target value or range (e.g., target skin resistance or conductance). As indicated supra, the particular target selected can vary somewhat depending upon the individual being treated and the nature of the substance being extracted. An AC signal is subsequently applied 54 to reach the desired target electrical state and to facilitate extraction of the substance across the tissue. As indicated above, application of an AC signal alone without a prepulse may require a longer period to reach the desired target. Nonetheless, application of the AC signal significantly increases transport over simple passive diffusion for the reasons discussed supra. Moreover, the AC signal by reversing polarity keeps the tissue depolarized and less susceptible to buildup of charged species at the surface of the tissue. The AC signal also maintains a relatively constant level of skin permeability that allows for relatively constant, controlled, predictable, and determinable extraction of the substance through the tissue.

During the time that the AC signal is applied, the electrical state of the tissue is measured 58, either continuously or periodically, to determine whether the electrical state of the tissue remains within the target range. If the electrical state is within the target range, the AC signals are applied without modification. If, however, the measured electrical state drifts outside the target range, then the AC signal is adjusted 60 to return the electrical state back within the target range. The AC signal is applied for a period sufficient to extract 56 the desired amount of substance across the tissue at a substantially constant rate after which the method ends 62.

2. AC plus Prepulse Protocol

Figure 2:
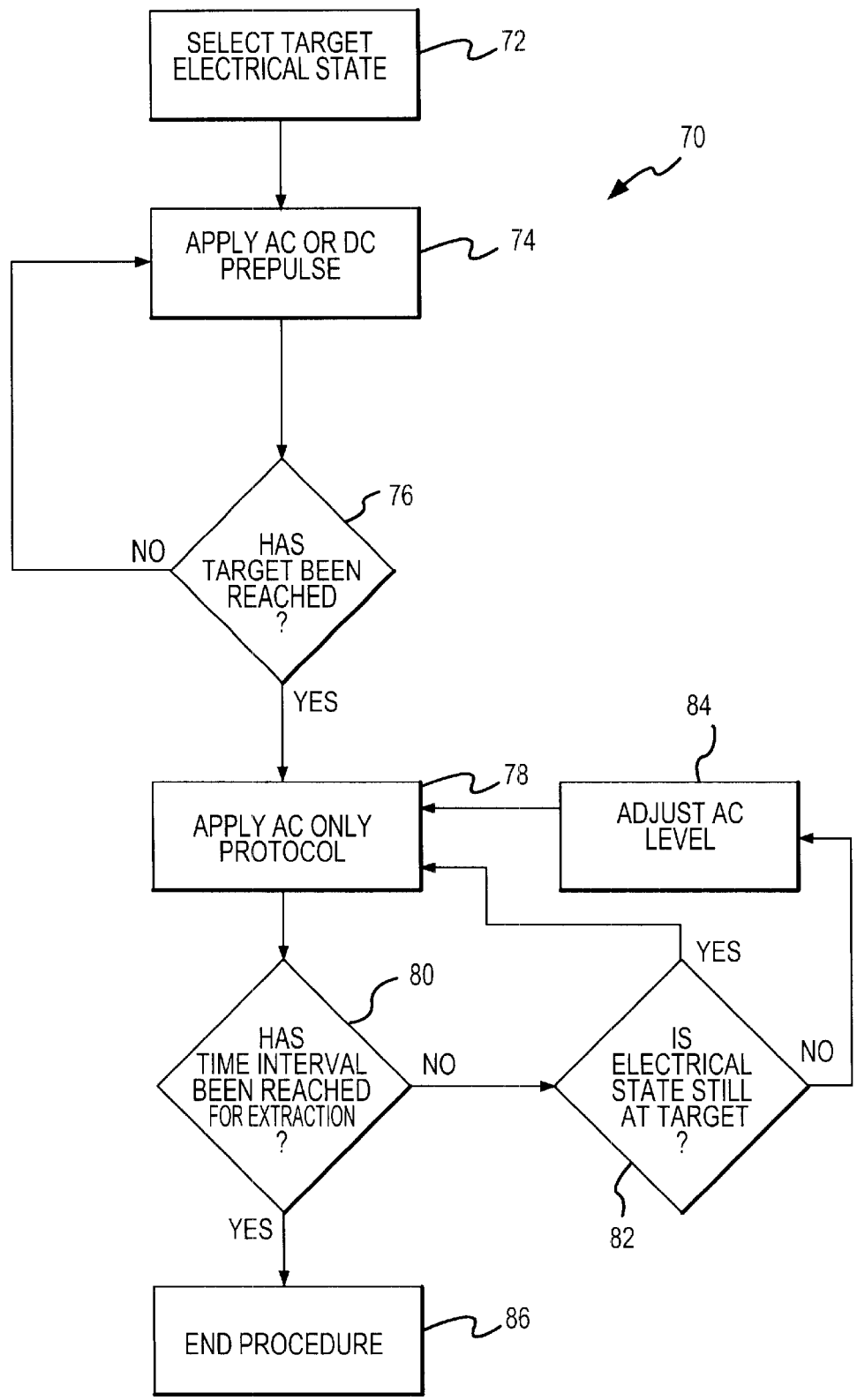
FIG. 2 is a schematic block diagram illustrating steps in a method utilizing an AC signal and a prepulse to extract a substance across a tissue as provided herein.

A schematic illustration of one AC plus prepulse method 70 is set forth in FIG. 2. With this particular approach, the selection 72 of a target electrical state is as described for the AC-only protocol and shown in FIG. 1. However, prior to application 78 of the AC signal, an AC or a DC prepulse is applied 74 to the tissue to relatively quickly achieve the selected electrical state. Once it has been determined that the target state has been reached 76, an AC signal is applied 78 to the tissue. The electrical state is monitored 82 continuously or periodically as described in the preceding section to maintain the target electrical state throughout the time period during which extraction occurs. The AC signal is adjusted 84 as needed to maintain the target state. Once the extraction period is completed 80, the procedure ends 86.

3. AC plus DC Offset

Figure 3:
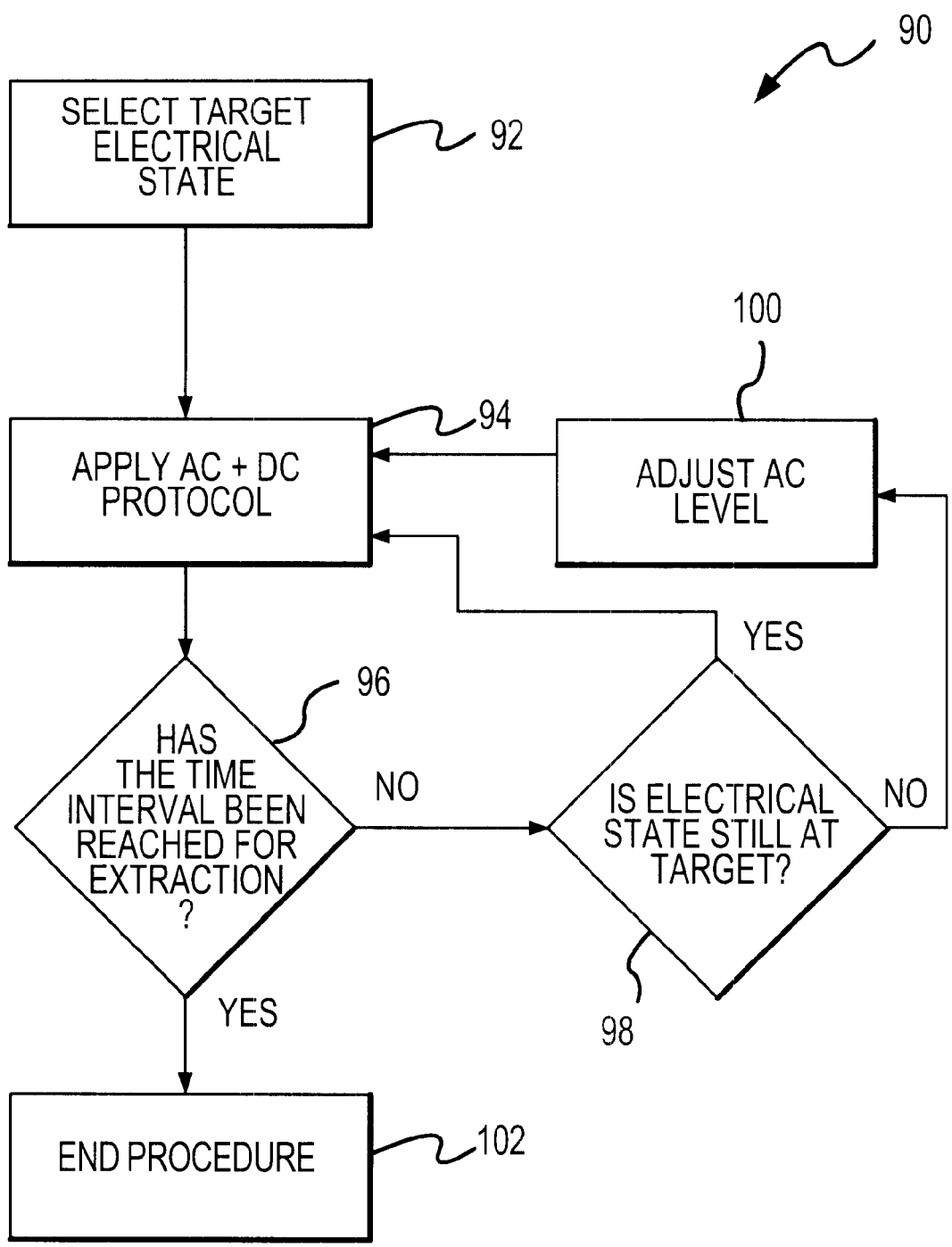
FIG. 3 is a schematic block diagram illustrating steps of a method utilizing an AC signal and a DC offset signal to extract a substance across a tissue as provided herein.

FIG. 3 illustrates the primary aspects of a method 90 utilizing an AC plus DC offset protocol. The initial stages of the method generally track those described for the AC-only protocol including selection 92 of a target electrical state. In this particular method, however, an AC signal and a DC offset signal are applied 94 to the tissue. The DC offset signal can be applied simultaneously with the application of the AC signal or any time during the treatment period. If it is determined 98 that the electrical state is no longer at the targeted value, the AC signal is adjusted 100 to return the electrical state to the target value or range. Such an adjustment is usually independent of the DC signal and is generally non-interfering to the DC driven transport. The DC signal is typically kept constant but can optionally be adjusted to change the extraction rate of the substance being transferred during the treatment. Once the desired amount of substance has been extracted 96, application of the AC and DC signals is terminated 102.

4. AC plus Prepulse plus DC Offset

Figure 4:
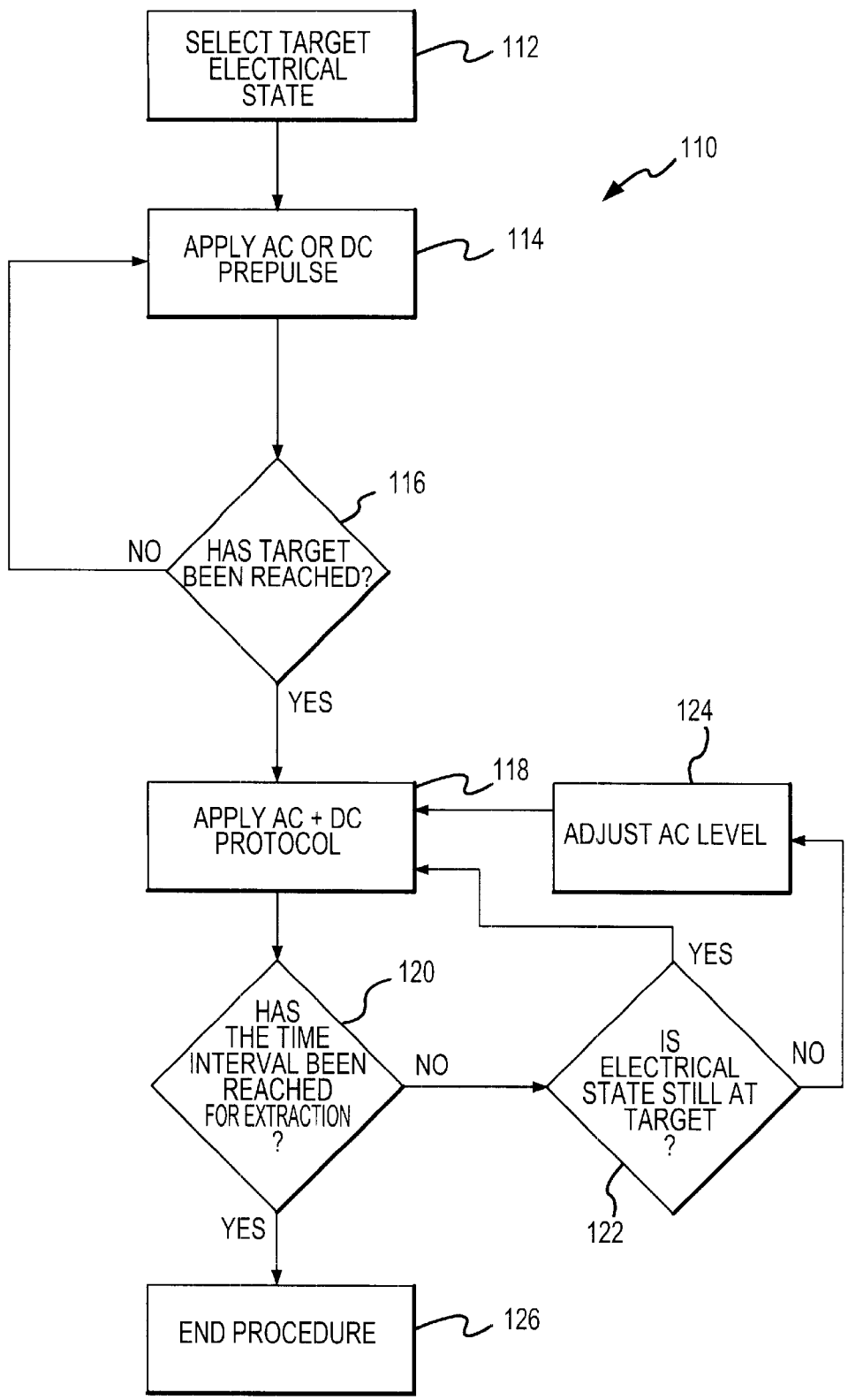
FIG. 4 is a schematic block diagram illustrating steps of one method utilizing a prepulse, an AC signal and a DC offset signal to extract a substance across a tissue as provided herein.

Certain methods 110 combine the prepulse and the DC offset signals with the AC signal (see FIG. 4). Such methods utilize the unique features of each type of signal to optimize extraction of a substance. As described supra, a target electrical state is selected 112 followed by application 114 of an AC or DC prepulse to quickly establish a selected electrical state correlated with an increased level of tissue permeability that promotes extraction of the substance. Once it is determined 116 that the target state has been reached, the AC signal and DC offset signal are applied 118, with the AC signal primarily functioning to maintain the target electrical state and the DC offset acting to promote transport of substance across the electroporated tissue. The electrical state is monitored 122. If the electrical state is found to vary from the target, the AC signal is adjusted 124 as required to return the electrical state to the target. Once the desired amount of substance has been extracted 120, the process is completed 126.

F. Process Subsequent to Extraction

The presence of a particular substance of interest in the reservoir can be detected utilizing a variety of techniques. For example, if a liquid is collected within the reservoir, the presence of a substance or substances of interest within the liquid can be detected using any of a variety of analytical techniques such as various chromatographic methods [e.g., high performance liquid chromatography (HPLC)], spectroscopic methods [e.g., infra-red spectroscopy (IR), nuclear magnetic resonance spectroscopy (NMR) and mass spectroscopy (MS)], electrochemical methods [e.g., electrical resistance and/or electrical potential], and enzymatic methods coupled with colorometric analysis or electrical potential changes. Combinations of analytical techniques can also be utilized [e.g., gas chromatography/mass spectroscopy (GC/MS)]. Detection of the substance can be either qualitative or quantitative.

The reservoir can include various agents that specifically react with one or more substances of interest to form a detectable product or complex. For example, the reservoir can include a dye that emits or absorbs light of a particular wavelength upon interaction with the substance(s). In yet other methods, an enzyme with specific activity for the analyte can be coupled with another enzyme with specific activity for another ligand capable of releasing electrons detectable by a sensor when metabolized by the second enzyme. For example, if the extracted substance is glucose, the enzyme can be glucose oxidase. The glucose oxidase can be coupled with peroxidases, which cause electron release that can be detected by a sensor. Various other sensors can be utilized to detect glucose, such as glucose selective electrodes (see, e.g., Solsky, R. L. (1988) *Anal. Chem.* 60:106R–113R) and various in situ analyses known in the art (e.g., colorimetric analyses).

The concentration of substance in the extraction reservoir can be correlated with the concentration of the substance in various ways. In some instances, mathematical algorithms established from a large population set or calibration procedures are utilized to correlate the two values.

G. Substances

The methods disclosed herein can be used in the extraction of a wide range of substances. The methods can generally be utilized to extract any substance that is in the system or body (e.g., circulating system, tissue system) of the subject and that can be transported across an electroporated tissue. When the tissue is human skin, the substance is either endogenous or one previously introduced into the body by some means. Thus, the substance can be molecules that are markers of disease states, pharmaceutical agents administered to the subject, substances of abuse, electrolytes, minerals, hormones, peptides, metal ions, nucleic acids, genes, and enzymes or any metabolites, conjugates, or other derivations of the aforementioned substances. In some instances, more than one substance is monitored at a time. Specific monitoring applications are described infra. The substances can be charged (negatively or positively), uncharged or neutral (e.g., zwitterionic substances with an equal number of opposite charges).

Substances that can be monitored further include, but are not limited to, oligosaccharides, monosaccharides (e.g., glucose), various organic acids (e.g., pyruvic acid and lactic acid), alcohols, fatty acids, cholesterol and cholesterol-based compounds and amino acids. A number of different substances that correlate with particular diseases or disease states can be monitored. For example, phenylalanine levels can be ascertained to assess treatment of phenylketonuria, which is manifested by elevated blood phenylalanine levels. Examples of metals that can be monitored include, but are not limited to, zinc, iron, copper, magnesium and potassium. Additional substances that can be extracted from humans are discussed in "Iontophoresis Devices for Drug Delivery," by Praveen Tyle, Pharmaceutical Research, vol. 3, no. 6, pp. 318–326.

The methods can be utilized to assess the concentration of various pharmacologically active agents that have been administered for either therapeutic or prophylactic treatment. Examples of such substances include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; antiinfective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; β-agonist; and tocolytic agents or active metabolites thereof.

IV. Extraction Systems

Figure 5:
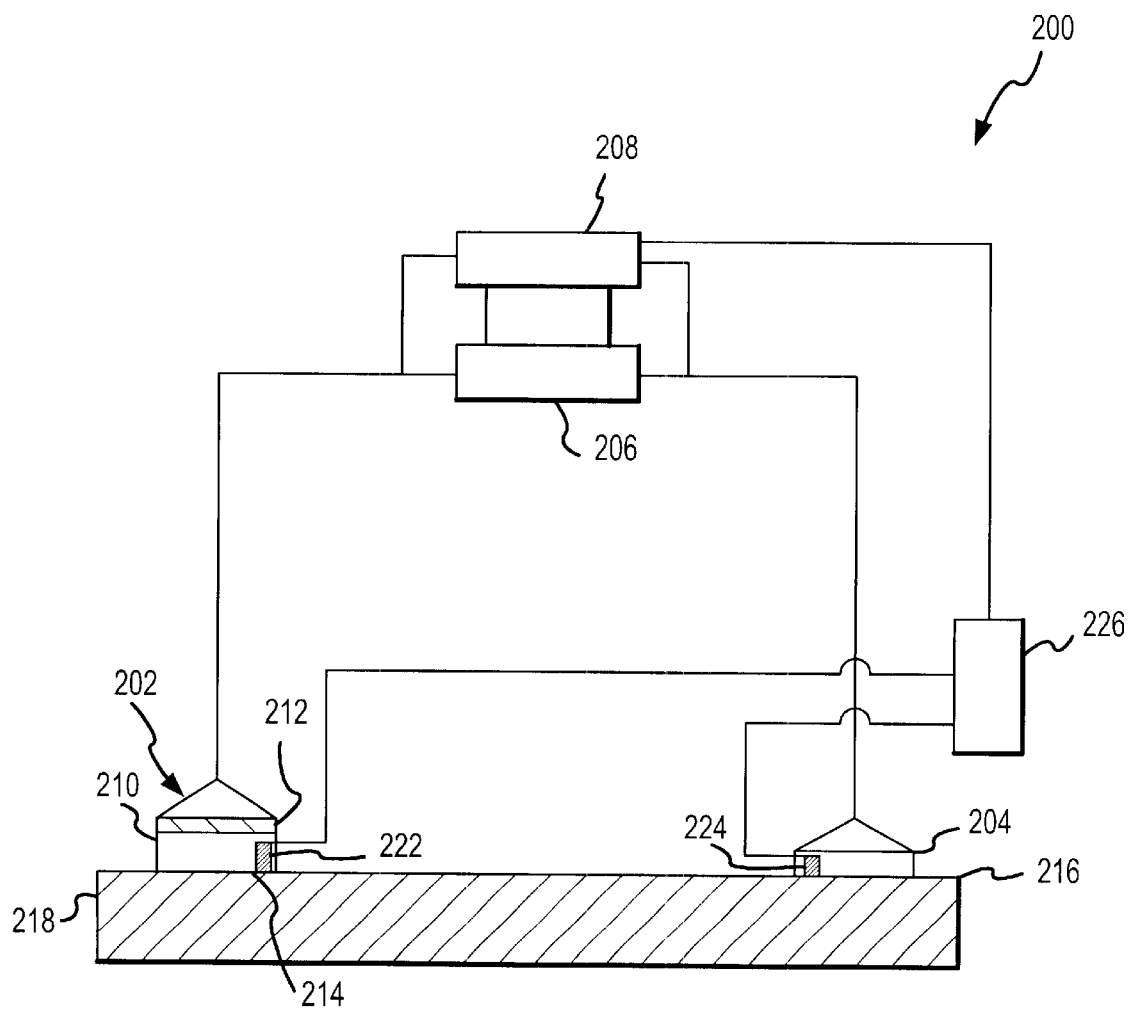
FIG. 5 is a schematic representation of an exemplary apparatus for extracting a substance across a tissue, such as extracting a metabolite or pharmacologically active agent across the skin of a patient.

One embodiment of an apparatus for performing the methods disclosed herein is represented schematically in FIG. 5. This system 200 for extracting substances across a tissue or body surface 218 generally comprises a first set of two electrodes 202, 204 electrically connected to a power source 206. The power source 206 can be a single source capable of delivering both an AC and a DC signal, or include two separate sources, one for delivering an AC signal and the other that delivers a DC signal. A circuit including the two electrodes 202, 204 and power source 206 is also connected to a controller 208 that monitors the electrical signals delivered to the electrodes 202, 204 and which can send signals to the power source 206 to alter the signals transmitted therefrom.

At least one of the electrodes 202,204 includes at least one reservoir (e.g., 210) and is electrically connected to a reservoir surface 212. Another surface 214 of the reservoir 210 is placed against a surface 216 of the tissue 218 (e.g., a patient's skin) and held in place, for example, by an adhesive or gel (not shown). The reservoir 210 is designed to receive one or more substances (e.g., metabolites or pharmaceutical agents, not shown) that are extracted across the tissue 218. The other electrode 204 of the pair is also placed in contact with a surface 216 of the tissue 218 and held in position with an adhesive or gel (not shown). This electrode 204 is positioned to allow for formation of a current that flows between the two electrodes 202, 204. When only an AC signal is applied to the tissue 218, the direction of current flow changes direction between the two electrodes on a period equal to the frequency of the applied current. When a DC offset signal is applied using the electrodes 202, 204, current flow is in the direction to enhance the transport of a charged or uncharged substance within the system of the individual receiving treatment towards at least one reservoir across the tissue 218.

The apparatus 200 can optionally include a second set or monitoring set of electrodes 222, 224 that are placed within the region of the tissue being electroporated to monitor the electrical state of the tissue 218 during extraction of the substance across the tissue. As indicated supra, the electrical state monitored is one that reflects the extent of tissue permeability or the state of electroporation (e.g., electrical resistance or electrical conductance). This second set of electrodes is optional because the first set of electrodes 202, 204 can be used to monitor the electrical state of the tissue 218. The monitoring electrodes 222, 224 can be attached to a separate monitor 226 as shown in FIG. 5, or optionally to the same controller 208 as the first set of electrodes 202, 204. If attached to a separate monitor 226, monitor 226 can send signals regarding the electrical state of the tissue 218 as measured by the second set of electrodes 222, 224 to controller 208.

The first set of electrodes 202, 204 utilized in applying the electrical signals can be of any of the standard types of electrodes utilized in iontophoresis. Some systems use nonpolarizable electrodes such as standard electrocardiograph electrodes manufactured from silver/silver chloride. Other suitable materials include gold, stainless steel and platinum. Multichannel dispersive electrodes can also be utilized in certain methods (see, e.g., U.S. Pat. No. 5,415,629).

When a DC offset signal is utilized, the electrode including the reservoir functions as either the cathode or anode depending upon the charge of the substance being extracted. In general, the anode receives the positive contribution of the DC offset signal, whereas the cathode receives the negative contribution of the DC offset signal. Consequently, if a DC offset signal is applied, negatively charged ions are extracted through the tissue and received in the reservoir which is part of the anode; positively charged ions are extracted across the tissue and received in the reservoir which is part of the cathode. Because the direction of electroosmotic flow is from the anode to the cathode at physiological pH, uncharged substances are extracted across the tissue and received in the reservoir, which is part of the cathode. It should be noted that when a DC offset is not utilized and the signal only consists of AC, there is no formal anode or cathode.

In some systems, it can be useful to include a reservoir at both electrodes 202, 204. For example, if only an AC signal is applied, agent can be extracted via diffusion into either reservoir. As described further infra, some methods using a DC offset involve reversing the direction of current flow at different time points. Reservoirs located at both electrodes 202, 204 can be useful in such methods because extraction from the system of the individual into both reservoirs can occur depending upon the direction of the DC signal. Two reservoirs can also be utilized to good effect if two different substances of opposite charge, or if a neutral and a negatively charged substance, are to be extracted. In such instances, differently charged substances are extracted into separate reservoirs.

In operation, initially the first set of electrodes 202, 204 are positioned and then an electrical signal delivered to the first set of electrodes 202, 204 via the power supply 206. The particular signals delivered depend upon which of the protocols disclosed supra are utilized. As indicated above, however, the various methods generally involve utilizing the power supply 206 to generate an AC signal of appropriate shape, duration, frequency and voltage to maintain a selected electrical state. If during the transport process, the electrical state deviates from the target electrical state as detected by the monitoring electrodes 222, 224, then the appropriate adjustments are made with the power supply 206 to vary the AC signal such that the electrical state is brought back to the target value or within the target range.

The controller 208 can be under microprocessor control. If the microprocessor-based controller determines, on the basis of signals from the monitoring electrodes 222, 224, that the electrical state has deviated from the target, it can signal the power source 206 to alter the AC signal so as to return the electrical state to the desired target. Such a controller can also include a safety shut off if it is determined that the electrical state of a patient's skin, for example, has reached an unacceptable level.

For methods utilizing either an AC or a DC prepulse, a prepulse of appropriate frequency, voltage and duration is generated by the power source 206 that is effective to reach the target electrical state. The monitoring electrodes 222, 224 can be utilized during this process to follow the progress towards the desired electrical state. Once this state is achieved, a signal is sent to the controller 208, which terminates generation of the prepulse and then generates the AC signal and/or the DC offset for application to the tissue.

As indicated above, in some methods the concentration of the substance within the individual's system is sufficiently higher than that on the other side of the tissue such that agent is transported through the electroporated region via passive diffusion. More typically, however, the power supply 206 is also utilized to generate a DC offset signal. This current drives the transport of a charged substance towards the electrode having an opposite charge or an uncharged substance from anode to cathode. However, in some procedures, the direction of the DC current flow is reversed between the first set of electrodes in order to reduce potential skin irritation, prevent electrochemical depletion of the nonpolarizable electrode, increase the surface area for extraction, and allow the biosensor to operate for longer periods of time.

Through the use of solid-state circuitry, the various foregoing elements such as signal extracting electrodes, power supply and reservoir can be included in a small, integrated device that can be conveniently worn by an individual without interfering with the individual's daily activities.

V. Exemplary Applications

The extraction methods provided herein can be used in a variety of applications, including the treatment of various disorders and diseases. Certain methods are used in the treatment of individuals who have elevated blood glucose levels. For example, some methods are utilized to monitor glucose levels within an individual on either a periodic or substantially constant basis. Such methods are useful in monitoring glucose levels in diabetics, for example. Instead of monitoring glucose levels directly, one can monitor a product formed during metabolism of glucose such as lactic acid and/or pyruvic acid.

The methods can be used in various diagnostic applications. For instance, the methods can be used to detect or monitor the presence of a substance within an individual's system that is correlated with a particular disease or disease state (i.e., a disease "marker"). As indicated above, phenylalanine levels can be monitored to assess risks for phenylketonuria, which is manifested by elevated blood phenylalanine levels. Another example is the monitoring of blood alcohol or illicit substances as part of a court ordered treatment program.

The methods also have utility in a variety of therapeutic applications. By way of example, some methods are utilized to track the level of one or more pharmaceutical agents administered to a patient (or metabolic products thereof) as a way to assess the current levels of active ingredient within the patient's system and to control the level within a patient's system.

In yet a further embodiment, the tracking of a patient's blood level of a therapeutic agent can be coupled with a drug delivery device to automatically keep the blood level of a narrow therapeutic window agent within tight tolerances. Thus, in such embodiments, certain systems as described supra can include a reservoir at one electrode for collecting a substance extracted from an individual's body and a second reservoir at the second electrode for delivering a desired agent. As a specific example, one system extracts glucose to monitor glucose levels and delivers insulin or another hypoglycemic agent as needed, once glucose levels become elevated.

The following example is provided to illustrate certain aspects of the methods disclosed herein and is not to be construed so as to limit the scope of the methods.

EXAMPLE

I. Experimental

A. Materials

Radiolabeled [$^3$H] mannitol and [$^{14}$C] tetraethylammonium bromide (TEA$^+$) were purchased from New England Nuclear (Boston, Mass.) and American Radiolabeled Chemicals (St. Louis, Mo.), respectively. Human epidermal membrane (HEM) was prepared by heat separation of split-thickness excised human skin. Phosphate buffered saline (PBS, pH 7.4) was prepared at an ionic strength of 0.1 M using reagent grade chemicals and deionized water.

B. Experimental Methods

1. General

Iontophoretic transport studies were carried out in a side-by-side two-chamber diffusion cell (diffusional surface area of around 0.8 cm$^2$ and chamber volume of 2 mL) with HEM at 37° C. The apparent permeability coefficients (P) in each experiment were calculated by:

$$P = \frac{1}{C_D A} \frac{dQ}{dt} \quad (1)$$

where A is the membrane surface area, t is time, Q is the amount of permeant transported into the receiver chamber, and $C_D$ is the concentration of permeant in the donor chamber. The pH of the solutions in the donor and receiver chambers was checked after each iontophoresis run to detect possible water hydrolysis.

2. Traditional Constant Current Methods

Constant current DC transport experiments were carried out at the current level of 0.13 mA/cm$^2$ using a constant current iontophoretic device (phoresor II Auto, Model No. PM 850, Iomed, Inc., Salt Lake City, Utah) with Ag—AgCl electrodes. HEM initial resistance was measured by applying 100 mV electrical potential across the membrane using a four electrode potential system (JAS Instrumental Systems, Inc., Salt Lake City, Utah) as described previously by Srinivasan et. al. (1989), Journal of Controlled Release; 10:157–165. HEM resistance during iontophoresis was measured by monitoring the electrical potential drop across the membrane using two flexible Luggin capillaries which were inserted into the donor and receiver compartments of the diffusion cells. Each of the Luggin capillaries contained a calomel electrode connected to a voltmeter. The HEM resistance could be determined during iontophoresis according the output current level and the voltmeter readings.

A trace amount of [$^{14}$C] TEA$^+$ and [$^3$H] mannitol was added to the donor chamber at the beginning of the experiment. One ml of sample was taken from the receiver chamber approximately every 30 minutes and replaced with the fresh PBS. A 10 µl sample was taken from the donor chamber every hour. Samples were mixed with 10 ml scintillation cocktail (Ultima Gold™, Packard Instrument Co., Meriden, Conn.) and assayed by a dual-labeled liquid scintillation counter (Parkard TriCarb™ Model 1900 TR Liquid Scintillation Analyzer).

3. AC+DC Offset Methods 5 volts DC was applied using the four electrode potentiostat system to reduce the skin electrical resistance to 2 kΩ, followed by a 50 Hz square-wave AC with 250 mV DC offset generated from a function generator (Model 4017, BK Precision, Placentia, Calif.). The electrical conductance of the membrane was monitored by an oscilloscope (Model 2211, Tektronix Inc., Beaverton, Oreg.). The output AC voltage was manually adjusted between 3 to 8 volts to keep the skin resistance at 2 kΩ (±10%) and the DC offset value was kept constant at 0.25 V during the entire period of the experiment. The same permeants and sampling protocol were used as described in the Constant Current Session.

4. AC+Passive Transport Methods (AC without DC Offset)

The same protocol was used to reduce the skin electrical resistance to 2 kΩ as described in the AC+DC Offset method. The DC prepulse was followed by a 50 Hz square-wave AC without the DC offset to keep the skin resistance at 2 kΩ (±10%) by manually adjusting the output AC voltage as described in the AC+DC Offset experiment session. Permeants and sampling protocol were the same as in the Constant Current and AC+DC Offset sessions as described above.

II. Results

A. Comparison of Traditional Constant Current DC Methods, and AC+DC Offset and AC without DC Offset Protocols The permeability coefficient (flux normalized by donor concentration) of mannitol and tetraethylammonium ion (TEA$^+$) through a human epidermal membrane was determined for a number of different samples according to the constant current DC method, the AC without DC Offset protocol and the AC+DC Offset protocol set forth in section I of this example. Mean values and standard deviation values were calculated from the results and are summarized in Tables 1 and 2 below.

The standard error of the means (SEM) indicates the amount of variability in the measured permeability values for each approach, and more specifically is the percentage of the mean that the standard deviation represents. Hence, the smaller the SEM, the smaller the standard deviation normalized to the mean and the less variability in the measured values.

As Table 1 shows, the traditional constant current DC only treatment produces relatively large SEM values for mannitol transport as compared to the SEM values for the new AC without DC Offset and AC+DC Offset methods. In addition, Table 2 demonstrates TEA$^+$ transport for the AC without DC Offset method, the AC+DC Offset method, and a traditional constant current DC method. Like mannitol transport, Table 2 shows the relatively large SEM value for DC only compared with the AC without DC Offset method or the AC+DC Offset method.

These results indicate that a significant reduction in variability of the electrical state of the tissue as measured by the permeability values was achieved utilizing either the AC without DC Offset method or the AC+DC Offset method for both uncharged permeants, such as mannitol, and charged permeants, such as TEA$^+$. Further, since these data represent the variability between skin samples excised from different human donors, we have demonstrated the superiority of AC without DC Offset or AC+DC iontophoresis for controlling inter-patient variability.

Table 3 below depicts the effect of various current profiles on the transport of mannitol and TEA$^+$. The last column of Table 3 shows the slope of the linear regression line of the best-fit line for all transport data points between 100 and 330 minutes. The slope of a line is defined as the rate of change of the relationship between two variables, in this case, permeant flux and time. Therefore, a slope of zero indicates that permeant flux is not changing with respect to time and the more positive (or negative) the slope, the more the flux is changing with time.

Table 3 shows that the change in flux with AC is roughly the same whether the target skin resistance is 2 or 4 kΩ for both the uncharged mannitol and the cationic TEA$^+$. It is also clear that the rate of change of the mannitol flux is 57% lower with the AC+DC Offset method compared with the AC without DC Offset method. The rate of change of mannitol flux with traditional constant current DC was 5.7- and 10-fold higher than the value obtained using the AC without DC Offset and the AC+DC Offset method, respectively. The rate of change of normalized TEA$^+$ flux was 7-fold higher with the AC+DC Offset method than the AC without DC Offset method. Lastly, the rate of change of the normalized TEA$^+$ flux was 3- and 20-fold higher with traditional constant current DC than with the AC+DC Offset method and AC without DC Offset method, respectively.

All of this data demonstrates that AC without DC Offset and AC+DC Offset iontophoresis produces less inter-subject variability (Tables 1 and 2) and less intra-subject variability (Table 3) than the traditional constant current DC only iontophoresis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

TABLE 1

Mannitol transport data. Mean and standard deviation represent permeability coefficient.

|  | 0.13 mA/cm$^2$ DC | AC (50 Hz) w/o DC Offset, target skin resistance = 2 kΩ | AC (50 Hz) with 0.25 V DC offset, target skin resistance = 2 kΩ |
|---|---|---|---|
| ONE TIME POINT (180 MIN) | | | |
| Number of samples | 7 | 4 | 6 |
| Mean | 1.5 × 10$^{-7}$ cm/s | 1.01 × 10$^{-7}$ cm/s | 1.7 × 10$^{-7}$ cm/s |
| Standard deviation | 0.9 × 10$^{-7}$ cm/s | 0.35 × 10$^{-7}$ cm/s | 0.2 × 10$^{-7}$ cm/s |
| Standard error of the mean | 61.3% | 34.8% | 8.8% |
| ALL DATA POINTS FROM 100 TO 330 MIN | | | |
| Number of Data Points (Number of skin samples) | 42 (7) | 28 (4) | 36 (6) |
| Mean | 1.6 × 10$^{-7}$ cm/s | 9.85 × 10$^{-8}$ cm/s | 1.6 × 10$^{-7}$ cm/s |
| Standard deviation | 1.0 × 10$^{-7}$ cm/s | 2.68 × 10$^{-8}$ cm/s | 0.3 × 10$^{-7}$ cm/s |
| Standard error of the mean | 60.6% | 27.2% | 18.8% |

TABLE 2

TEA$^+$ transport. Mean and standard deviation represent permeability coefficient.

|  | 0.13 mA/cm$^2$ DC | AC (50 Hz) w/o DC Offset, target skin resistance = 2 kΩ | AC (50 Hz) with 0.25 V DC offset, target skin resistance = 2 kΩ |
|---|---|---|---|
| ONE TIME POINT (180 MIN) | | | |
| Number of samples | 8 | 4 | 7 |
| Mean | 4.7 × 10$^{-6}$ cm/s | 9.9 × 10$^{-7}$ cm/s | 6.2 × 10$^{-6}$ cm/s |
| Standard deviation | 1.8 × 10$^{-6}$ cm/s | 0.7 × 10$^{-7}$ cm/s | 1.0 × 10$^{-6}$ cm/s |
| Standard error of the mean | 38.3% | 6.8% | 16.1% |
| ALL DATA POINTS FROM 100 TO 330 MIN | | | |
| Number of Data Points (Number of samples) | 48 (8) | 28 (4) | 42 (7) |
| Mean | 4.7 × 10$^{-6}$ cm/s | 1.08 × 10$^{-6}$ cm/s | 6.0 × 10$^{-6}$ cm/s |
| Standard deviation | 1.7 × 10$^{-6}$ cm/s | 0.24 × 10$^{-6}$ cm/s | 0.9 × 10$^{-6}$ cm/s |
| Standard error of the mean | 36.2% | 22.5% | 15.0% |

TABLE 3

Normalized flux data for mannitol and TEA$^-$.

| Current Type | AC Frequency | DC offset | Target Skin Resistance | Slope (cm sec$^{-1}$ min$^{-1}$) |
|---|---|---|---|---|
| NORMALIZED MANNITOL FLUX | | | | |
| AC | 50 Hz | — | 2 kΩ | 7 × 10$^{-11}$ |
| AC | 50 Hz | — | 4 kΩ | 7 × 10$^{-11}$ |
| AC + DC | 50 Hz | 250 mV | 2 kΩ | 4 × 10$^{-11}$ |
| 0.13 mA/cm$^2$ DC | — | — | — | 4 × 10$^{-10}$ |
| NORMALIZED TETRAETHYL AMMONIUM (TEA$^+$) FLUX | | | | |
| AC | 50 Hz | — | 2 kΩ | 3 × 10$^{-10}$ |
| AC | 50 Hz | — | 4 kΩ | -3 × 10$^{-10}$ |
| AC + DC | 50 Hz | 250 mV | 2 kΩ | 2 × 10$^{-9}$ |
| 0.13 mA/cm$^2$ DC | — | — | — | 6 × 10$^{-9}$ |

What is claimed is:

1. A method for extracting a substance from a body through a tissue, comprising:

(a) supplying one or more electrical signals, the one or more electrical signals comprising an AC signal;

(b) applying the AC signal to the tissue; and (c) adjusting the AC signal so as to maintain a substantially constant electrical state within a region of the tissue, wherein maintenance of the substantially constant electrical state facilitates extraction of the substance.

2. The method of claim 1, wherein the AC signal is adjusted to maintain a substantially constant state of electroporation in the region of the tissue throughout the time period in which the substance is extracted.

3. The method of claim 1, wherein the electrical state is electrical conductance or electrical resistance and the AC signal is adjusted to maintain a substantially constant electrical conductance or electrical resistance in the region of the tissue throughout the time period in which the substance is extracted.

4. The method of claim 1, wherein the waveform of the AC signal is symmetric.

5. The method of claim 1, wherein the waveform of the AC signal is asymmetric.

6. The method of claim 1, wherein the shape of the AC signal waveform is square, sinusoidal, saw-tooth, triangular or trapezoidal.

7. The method of claim 1, wherein the frequency of the AC signal is at least about 1 Hz.

8. The method of claim 1, wherein the frequency of the AC signal is in the range of about 1 Hz to about 1 kHz.

9. The method of claim 1, wherein the frequency of the AC signal is in the range of about 1 kHz to about 30 kHz.

10. The method of claim 1, wherein the one or more electrical signals further comprise an electrical prepulse applied to the tissue prior to the AC signal to induce electroporation within the region.

11. The method of claim 1, wherein the voltage of the electrical prepulse is in the range of about 1 to about 90 V.

12. The method of claim 11, wherein the voltage of the electrical prepulse is in the range of about 5 to about 20 V.

13. The method of claim 11, wherein the voltage of the electrical prepulse is in the range of about 20 to about 40 V.

14. The method of claim 11, wherein the voltage of the electrical prepulse is in the range of about 40 to about 90 V.

15. The method of claim 11, wherein the electrical prepulse is a DC prepulse.

16. The method of claim 11, wherein the electrical prepulse is an AC prepulse.

17. The method of claim 12, wherein the electrical prepulse is a DC prepulse.

18. The method of claim 12, wherein the electrical prepulse is an AC prepulse.

19. The method of claim 1, wherein extraction of the substance is via passive diffusion through the electroporated region.

20. The method of claim 1, wherein.
   (a) the one or more electrical signals further comprise a DC offset signal; and
   (b) the applying step comprises applying the DC offset signal to the tissue, wherein the DC offset signal is effective to promote extraction of the substance through the region.

21. The method of claim 20, wherein the DC offset signal is applied substantially continuously during extraction of the substance and is of a voltage or current effective to control the rate of extraction of the substance through the region.

22. The method of claim 20, wherein the voltage of the DC offset signal is in the range of about 0.1 V to about 5 V or the current range of about 0.01 to about 0.5 mA/cm$^2$.

23. The method of claim 20, wherein the AC signal and the DC offset signal are provided simultaneously.

24. The method of claim 20, wherein the DC offset signal is applied after initiation of the AC signal.

25. The method of claim 20, wherein the DC offset signal is applied utilizing two electrodes in contact with the tissue and the direction of current flow of the DC offset signal is periodically reversed between the two electrodes.

26. The method of claim 1, wherein:
   (a) the one or more electrical signals further comprise an electrical prepulse and a DC offset signal;
   (b) applying comprises
      (i) applying the electrical prepulse to the tissue prior to the AC signal to induce electroporation within the region; and
      (ii) applying the DC offset signal to the tissue, wherein the DC offset signal promotes extraction of the substance through the region.

27. The method of claim 26, wherein the voltage of the electrical prepulse is in the range of about 1 to about 90 V.

28. The method of claim 27, wherein the electrical prepulse is a DC prepulse.

29. The method of claim 27, wherein the electrical prepulse is an AC prepulse.

30. The method of claim 26, wherein the DC offset signal is applied substantially continuously during extraction of the substance and is of a voltage or current effective to maintain a substantially constant rate of extraction of the substance through the region.

31. The method of claim 26, wherein the DC offset signal is applied utilizing two electrodes in contact with the tissue and the direction of current flow of the DC offset signal is periodically reversed between the two electrodes.

32. The method of claim 3, wherein the conductance or resistance within the region is maintained within a range that is approximately 20% of a target conductance or resistance.

33. The method of claim 32, wherein the range is approximately 10% of the target conductance or resistance.

34. The method of claim 33, wherein the range is approximately 5% of the target conductance or resistance.

35. The method of claim 34, wherein the range is approximately 1% of the target conductance or resistance.

36. The method of claim 1, wherein the tissue is human skin.

37. The method of claim 1, wherein the tissue is a human mucosal membrane.

38. The method of claim 1, wherein the tissue is an animal tissue other than a human tissue.

39. The method of claim 1, wherein the tissue is a plant tissue.

40. The method of claim 1, wherein the region has an area in the range of about 1 cm$^2$ to about 200 cm$^2$.

41. The method of claim 40, wherein the region has an area in the range of about 5 cm$^2$ to about 100 cm$^2$.

42. The method of claim 41, wherein the region has an area in the range of about 5 cm$^2$ to about 30 cm$^2$.

43. The method of claim 1, wherein the substance is an uncharged substance.

44. The method of claim 43, wherein the substance is glucose.

45. The method of claim 43, wherein the substance is ethanol.

46. The method of claim 1, wherein the substance is charged.

47. The method of claim 46, wherein the substance is negatively charged.

48. The method of claim 46, wherein the substance is positively charged.

49. The method of claim 1, wherein the substance is a substance correlated with a metabolic disorder.

50. The method of claim 49, wherein the substance is phenylalanine.

51. A method for extracting a substance from the body of a human patient through a tissue, comprising:
   (a) supplying one or more electrical signals, the one or more electrical signals comprising an AC signal;
   (b) applying the AC signal to the tissue, wherein the tissue is human skin or mucosal tissue; and (c) adjusting the AC signal so as to maintain a substantially constant state of electroporation within a region of the tissue throughout the time during which extraction occurs, wherein maintenance of the substantially constant state of electroporation promotes extraction of the substance.

52. The method of claim 51, further comprising applying an electrical prepulse applied to the tissue prior to the AC signal to induce electroporation within the region.

53. The method of claim 51, further comprising applying a DC offset signal effective to promote extraction of the substance through the region.

54. The method of claim 52, further comprising applying a DC offset signal effective to promote extraction of the substance through the region.

* * * * *